US012582744B2

(12) United States Patent
  Raut et al.

(10) Patent No.: US 12,582,744 B2
(45) Date of Patent: Mar. 24, 2026

(54) DRESSINGS COMPRISING PLATELET LYSATE

(71) Applicant: Arteriocyte, Inc., Hopkinton, MA (US)

(72) Inventors: Vivek Prabhakar Raut, Ashland, MA (US); Meghan Elizabeth Samberg, Upton, MA (US); Kolby Luke Day, Millcreek, UT (US); Brian Roy Barnes, Southborough, MA (US); Christopher Ronald Rathbone, San Antonio, TX (US); Patrick Patterson, Framingham, MA (US); Donald Jude Brown, Hopkinton, MA (US); Justin Jeffrey Baker, Gates Mills, OH (US)

(73) Assignee: ARTERIOCYTE, INC, Hopkinton, MA (US)

( * ) Notice: Subject to any disclaimer, the term of this patent is extended or adjusted under 35 U.S.C. 154(b) by 0 days.

(21) Appl. No.: 18/202,377

(22) Filed: May 26, 2023

(65) Prior Publication Data

US 2023/0338608 A1      Oct. 26, 2023

Related U.S. Application Data

(60) Division of application No. 16/234,708, filed on Dec. 28, 2018, now abandoned, which is a continuation-in-part of application No. PCT/US2017/039918, filed on Jun. 29, 2017.

(60) Provisional application No. 62/356,163, filed on Jun. 29, 2016.

(51) Int. Cl.
  *A61L 15/40*      (2006.01)
  *A61F 13/00*      (2006.01)
  *A61L 15/44*      (2006.01)

(52) U.S. Cl.
  CPC ........ *A61L 15/40* (2013.01); *A61F 13/00063* (2013.01); *A61L 15/44* (2013.01); *A61L 2300/404* (2013.01); *A61L 2300/418* (2013.01); *A61L 2400/04* (2013.01)

(58) Field of Classification Search
  CPC ...... A61L 15/40; A61L 15/44; A61L 2400/04; A61L 2300/418
  See application file for complete search history.

(56) References Cited

U.S. PATENT DOCUMENTS 9,682,104 B2 *  6/2017  Patel .................... A61K 9/0078

OTHER PUBLICATIONS

Mori et al. "Calcium alginate particles for the combined delivery of platelet lysate and vancomycin hydrochloride in chronic skin ulcers", J. International Journal of Pharmaceutics, 461 (2014) 505-513 (Year: 2014).*

* cited by examiner

*Primary Examiner* — James W Rogers
(74) *Attorney, Agent, or Firm* — Lippes Mathias LLP

(57)      ABSTRACT

A dressing comprises a delivery vehicle and platelet lysate. The dressing can also include an antimicrobial agent, a hemostatic agent, and a binder. It is contemplated that the dressing can be used for expediting hemostasis, improving antimicrobial activity, minimizing fluid loss, and accelerating wound healing when applied to a wound. The dressing would be useful in applications including military in-theater medical care and for conditions such as diabetic foot ulcers, as well as other applications.

7 Claims, 8 Drawing Sheets

DRESSINGS COMPRISING PLATELET LYSATE

CROSS-REFERENCE TO RELATED APPLICATIONS

This application is a divisional of U.S. patent application Ser. No. 16/234,708, filed on Dec. 28, 2018, which is a continuation-in-part of PCT Application Number PCT/US17/39918, filed Jun. 29, 2017, which claims priority to U.S. Provisional Patent Application Ser. No. 62/356,163, filed on Jun. 29, 2016, which is hereby fully incorporated by reference.

BACKGROUND

The present disclosure relates to dressings that can be used to simultaneously address complex trauma, namely blood loss, incidence of infection, prevention of wound progression, tissue preservation and restoration, revascularization, and wound healing. Such technology can be useful in military theatres, humanitarian assistance, disaster relief operations, and treatment of acute and chronic conditions affecting military and civilian populations. The dressings include human platelet lysate, and are useful for various applications and purposes.

New products that address critical aspects of traumatic wound care and can be easily used and deployed in large numbers must be developed. Desirably, such products can be used in the first hours post-injury with the goal of preventing secondary medical crises arising from blood loss, wound colonization, and delayed wound healing.

Severe wounds can be incurred in many different situations. For example, the use of improvised explosive devices (IEDs) has introduced medical challenges related to severe blast-induced injuries. IEDs use incendiary materials and are frequently contaminated with soil or sewage due to their source materials and/or placement. As a result, severe burns and lacerations with consequential infection are common. The loss of tissue viability and high incidence of infection has contributed to elevated limb amputation rates in military personnel who survive IED-induced injuries. The Boston Marathon incident in 2013 was an example of the use of IEDs on United States soil to inflict mass casualties. Humanitarian assistance and disaster relief operations, both military and civilian, also encounter medical situations in which traumatic wound care is provided.

Similar concerns arise in the treatment of diabetic foot ulcers, which is one of several complications of diabetes that markedly impairs quality of life, shortens lifespan, and constitutes an enormous societal economic burden. Diabetic foot ulcers (DFUs) are one of the most common and severe complications of diabetes and are now the leading cause of hospitalization in diabetic patients. Persons with diabetes have a 15% to 25% chance of developing a DFU during their lifetime, and a 50% to 70% recurrence rate over the ensuing 5 years. A significant amount of healthcare resources is spent on the management of DFUs, including emergency room visits, antibacterial medications, amputations, and a multitude of other therapies directed at chronic, non-healing wounds. Various estimates indicate that the cost of DFU treatment consumes 25 to 50% of the total cost of all diabetes treatment. Even more significantly, patients who develop a DFU have a 5% to 8% probability of suffering a major amputation in the first year, and DFUs precede 85% of all lower-limb amputations. Unfortunately, 45% to 55% of these patients die within 5 years of the amputation.

Multiple large-scale studies of patient self-reported quality of life have shown that limb loss has a larger negative impact on quality of life than any other complication of diabetes, including end-stage renal disease or blindness. In addition to the loss of mobility and independence, depression and anxiety are more prevalent among people with diabetes who have experienced limb loss.

One of the most important cost-saving considerations in caring for DFU patients is expeditious and complete wound healing to reduce the risk of infections and amputation. Standard management strategies for healing DFUs include surgical debridement of the wound, management of any infection with moist dressing changes, revascularization procedures when indicated, and off-loading of the ulcer. Despite a clearer understanding of the causal factors leading to limb loss and an increasing consensus on the management of various aspects of diabetic foot care in recent years healing rates for DFUs remain frustratingly low. Generally, healthcare practitioners strive to reduce the wound size by approximately 50% within 4 weeks. Unfortunately, current treatments result in healing rates of approximately 25% after 12 weeks and 30% after 20 weeks.

Only a small handful of advanced wound care technologies have shown some efficacy in accelerating DFU healing in large, prospective, randomized clinical trials. These include the application of becaplermin (Regranex®), a topical gel containing recombinant human platelet derived growth factor-BB (PDGF-BB); and two living skin equivalents: a bilayered skin substitute (Apligraf®) and a human fibroblast-derived dermal substitute (Dermagraft®). Disappointingly, these interventions provide only moderate improvement over standard treatments (generally only 15-20%), are considerably more expensive, and are associated with significant safety concerns. For example, becaplermin increased the risk of cancer mortality in patients. Other interventions, including hyperbaric oxygen and negative pressure devices, have shown promise in promoting DFU healing, but have yet to be tested in large clinical trials.

BRIEF DESCRIPTION

The present disclosure relates to various dressings that are formed from a delivery vehicle and human platelet lysate (hPL). The dressings permit the application of various materials for protecting a wound, and can also be used in other applications. In some particular embodiments, the dressings are in the form of bandages that can be used to expedite hemostasis, improve antimicrobial activity, minimize fluid loss, and accelerate wound healing. The bandage is comprised of hPL and may also include a substrate, an antimicrobial agent, a hemostatic agent, and/or a binding agent. Methods to control the release of all components are also disclosed herein. The bandages can provide sustained and/or controlled delivery of human derived growth factors from the hPL as well as agents to prevent infection and/or blood loss. The bandage is designed to be resilient and versatile with a long shelf life that is not affected by a broad range of environmental conditions. This provides an acute wound care covering that is readily deployable when needed and also readily available to care facilities for the treatment of chronic conditions such as diabetic foot ulcers (DFUs). In other embodiments, the dressings are in the form of liquids, creams, gels, shampoos, foams, or aerosols.

Disclosed herein in various embodiments are dressings comprising of hPL. It is particularly contemplated that the hPL is allogeneic human platelet lysate. The dressing also contains a delivery vehicle for the hPL.

In some specific embodiments, a substrate may be employed for the delivery vehicle, such as woven or non-woven fibers or gauze. The hPL can be applied as a coating on the delivery vehicle and/or impregnates the delivery vehicle. In others, the delivery vehicle is a hydrogel. In further embodiments, the delivery vehicle is human or animal tissue that may contain skin or bone grafts, or can be a powder or a sheet prepared from naturally or artificially derived materials such as collagen, alginate, cellulose, gelatin or combinations thereof. In others, the delivery vehicle is a powder. When the delivery vehicle includes a liquid carrier, the resulting dressing can be in the form of a shampoo, cream, or gel depending on the addition of other ingredients (e.g. surfactant, wax, gelling agent). In yet others, the delivery vehicle is a pressurized gas, and the dressing is in aerosol or foam form.

The dressing may further comprise an antimicrobial agent. The antimicrobial agent may contain silver, such as silver sulfadiazine, silver nitrate, or silver chloride. In alternative embodiments, the antimicrobial agent can be any antibiotic or iodine, chlorhexidine, vancomycin, bacitracin, ciprofloxacin, gentamycin, honey, or fish skin. The dressing can alternatively further comprise an antifungal agent.

In other embodiments, the dressing may further comprise a hemostatic agent. The hemostatic agent can be kaolin, chitosan, a zeolite, or a styptic such as anhydrous aluminum sulfate.

The dressing may further comprise an excipient binder. The binder can be glycerol, casein, acacia gum, xanthan gum, corn starch, wheat starch, cellulose, gelatin, pectin, chitosan, dextran, or albumin.

In particular embodiments, the dressing further comprises a combination of an antimicrobial agent and a hemostatic agent. The hPL, the antimicrobial agent, and the hemostatic agent can be dispersed in a single layer. Alternatively, the hPL, the antimicrobial agent, and the hemostatic agent may each form a separate layer.

As previously mentioned, the dressing may include a delivery vehicle that can be a powder or a sheet prepared from naturally or artificially derived materials such as collagen, alginate, cellulose, gelatin or a combination of thereof. The weight ratio of the hPL to the delivery vehicle may range from about 0.25% to about 90%.

Also disclosed herein are methods of making a bandage, comprising: combining a substrate with a solution that comprises hPL to obtain an impregnated substrate; freezing the impregnated substrate; and lyophilizing the impregnated substrate to obtain the bandage. The solution may contain only the hPL, or may also contain other constituents.

The methods may further comprise sterilizing the bandage using radiation or electron beam, or ultraviolet (UV) light.

As explained above, the bandage can further contain an antimicrobial agent, a hemostatic agent, and/or a binder, in any combination. The solution with which the substrate is combined may also contain these ingredients. A combination of constituents or an impregnated substrate may be frozen at a temperature below −70° C. prior to lyophilization.

Also disclosed are methods of making a dressing, comprising: mixing a hydrogel matrix with lyophilized (hPL); and gelling the hydrogel matrix with a liquid to obtain the bandage. Again, the hydrogel matrix may comprise any natural or artificially-derived material, such as carboxymethylcellulose, collagen, fibrin, alginate, poly(lactic-co-glycolic acid), or polyethylene glycol. The weight ratio of the hPL to the hydrogel matrix may range from about 0.25% to about 90%. The liquid may be a buffered saline or water. The hydrogel solution may have a pH in the range of 3 to 9. The hydrogel gelling may occur at a temperature between 20° C. and 37° C. The gelling may occur instantaneously, or be delayed for a period of up to 168 hours.

These and other non-limiting aspects and/or objects of the disclosure are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 7A is a graph of clot resistance versus time. A higher absolute value at a shorter time is more desirable. FIG. 7B is a table showing various data on clot formation. FIG. 7C is a picture of a bandage with kaolin and hPL applied thereon. FIG. 7D is a bar graph comparing the size of bandages at different temperatures before and after addition of hPL. FIG. 7E is a graph showing the PDGF-BB delivery amount over time for the bandages.

FIG. 10A is a baseline wound image. FIG. 10B is an image of the wound after 2 weeks of hPL-collagen bandage application. FIG. 10C is an image of the wound after 12 weeks of hPL-collagen bandage application to the wound.

FIG. 11A is a baseline picture.

FIG. 11B is a picture after 5 days of hPL-collagen bandage application. FIG. 11C is a picture after 16 days of application.

DETAILED DESCRIPTION

Figures 1, 2, 3:
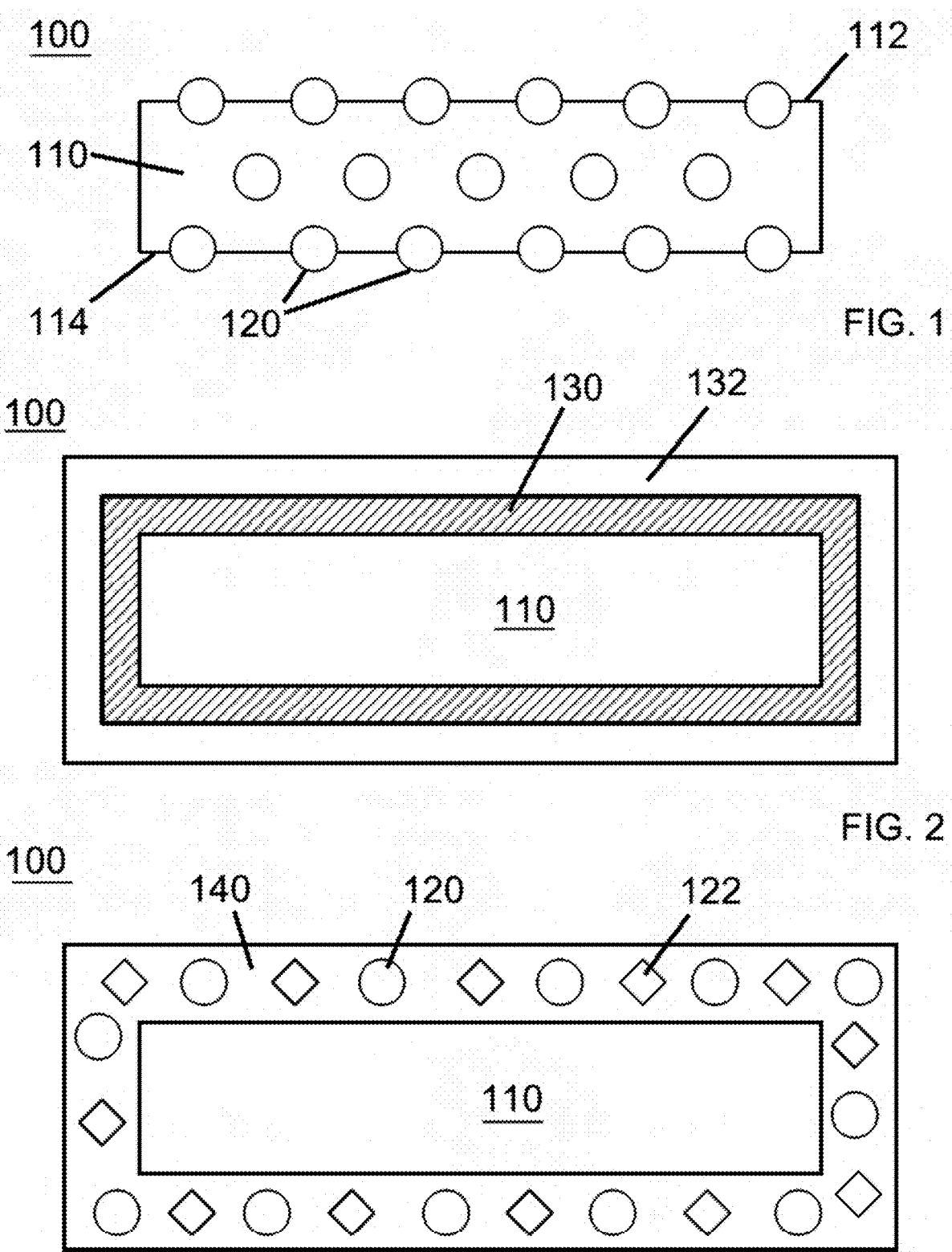
FIG. 1 is a cross-sectional diagram of a bandage that comprises a substrate and human platelet lysate (hPL) applied thereon. At least a portion of the hPL is on the surface of the substrate, and additional hPL may be impregnated within the substrate.
FIG. 2 is a cross-sectional diagram of a dressing that comprises a substrate and both human platelet lysate and a hemostatic agent applied thereon.
FIG. 3 is a cross-sectional diagram of a dressing that comprises a substrate and both human platelet lysate and an antimicrobial agent applied thereon.

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value. For example, the term "about 2" also discloses the value "2" and the range "from about 2 to about 4" also discloses the range "from 2 to 4."

In the context of this disclosure, the term "blood" is used generally to refer to whole blood, which is a water-based fluid containing diverse solutes, suspended polypeptides, growth factors, and blood cells. Examples of blood cells are white blood cells, red blood cells and thrombocytes. White blood cells (leukocytes) are immunocompetent cells in the circulation of blood characterized by their central role in maintaining the humoral and innate immune systems. Red blood cells (erythrocytes) are the major oxygen carrying cells in the blood. The thrombocytes (platelets) are smaller than both white and red blood cells and mediate certain types of coagulation of blood. In some examples, the blood is mammalian blood, such as for example human blood.

The term "plasma" refers to the yellow liquid component of whole blood, in which the blood cells in whole blood would normally be suspended. Put another way, plasma is whole blood minus the blood cells. Plasma is mostly water and comprises dissolved proteins, glucose, clotting factors, mineral ions, hormones and carbon dioxide. Plasma may be prepared by spinning a tube of fresh blood containing an anti-coagulant in a centrifuge until the blood cells fall to the bottom of the tube. The plasma is then poured or drawn off from the blood cells.

The term "substrate" is used herein to refer to a material that is in the solid phase at room temperature, and that provides a surface upon which other materials may be adhered. The term "liquid" refers to a material that is in the liquid phase at room temperature and that provides a medium in which other materials may be suspended or dissolved, e.g. water.

The present disclosure describes multiple ingredients (human platelet lysate, antimicrobial agent, hemostatic agent, etc.) as being present "within" or "upon" or "on" the delivery vehicle. These terms are intended to describe the ingredient as being present on any location of the delivery vehicle. For example, the ingredients can be located on the surface of the delivery vehicle, or be impregnated within the delivery vehicle, for example when the delivery vehicle is made up of various fibers or is a gel.

The present disclosure relates to dressings that contain human platelet lysate (hPL). The dressings come in several different forms, depending on their application. In particular embodiments, the dressings are in the form of bandages, also known as hemostatic devices, which can be applied to bleeding wounds to promote hemostasis, tissue viability, and infection control. The presence of hPL on the bandage results in sustained delivery of growth factors to the wound area. Other compositions that include hPL are also described, which can be useful for other applications.

In this regard, platelets contain several bioactive components that contribute to the wound healing cascade. These include growth factors, attachment factors, and enzymes that have pro-regenerative, pro- and anti-inflammatory, immunomodulatory, and/or anti-microbial activities. Many studies have shown that topical application of growth factors, such as transforming growth factor beta (TGF-$\beta$), PDGF, and basic fibroblast growth factor (bFGF), can accelerate wound closure in animal models.

Autologous platelet rich plasma (PRP), a preparation of highly concentrated platelets produced from a patient's own blood, has been used extensively in the treatment of chronic wounds and is also being investigated as a burn wound treatment. PRP is typically applied as a gel for wound healing applications, after formation of a fibrin clot via addition of thrombin and/or $CaCl_2$). Addition of thrombin also activates platelets, causing them to release their entire cargo of wound healing factors into the gel. PRP gel contains the full range of platelet-derived factors, and thereby closely mimics the healing milieu present in acute wounds. However, PRP loses efficacy after only a few days, and thus is not suitable as an "off-the-shelf" product that can be stored over the long term. Also, the total volume of whole blood product from which PRP is derived is limited; therefore, PRP is not practical for wounds that are larger than 25% total body surface area (TBSA).

With respect to diabetes, the ability of endogenous platelets to stimulate wound healing is highly dependent on the overall health of the patient, and platelets from diabetic patients may show reduced wound healing capacity. Despite the fact that many growth factors are overexpressed in diabetic patients, the glycation levels are significantly increased under hyperglycemic conditions as compared to healthy individuals. Glycation of growth factors has been shown to reduce their biological activity in vitro, and would be expected to impact their ability to stimulate wound healing in vivo. For instance, glycation of bFGF in vitro occurs rapidly within 24 hours in the presence of elevated levels of glucose-6-phosphate, resulting in a significant reduction in the ability of bFGF to bind to the tyrosine kinase receptor and activate signal transduction pathways responsible for both mitogenesis and capillary formation in endothelial cells, which ultimately impairs angiogenesis and wound healing. Similarly, the proliferation and migration of human dermal fibroblasts are significantly reduced in glycated PDGF-BB treated cells compared to native PDGF-BB treated cells.

Platelet lysate technology provides an opportunity to harness the bioactive properties of platelets in a form that is conducive to long-term storage. Human platelet lysate (hPL) is a cell-free formulation of platelet-derived factors produced via a simple freeze-thaw lysis process. Generally, during processing of the platelets, all clotting factors and cellular membranes are removed via centrifugation and filtration, leaving behind a growth factor-rich preparation with a very low content of white blood cell antigens that could cause immune responses. Similar to activated PRP, hPL contains a plethora of growth factors known to enhance cell proliferation and angiogenesis, including PDGF, bFGF, VEGF, TGF-β, and EGF. hPL also provides a supraphysiological dose of platelet factors. When made from blood from a single donor or from pooled blood that comes from a large number of different donors, the product is known as allogeneic hPL.

The beneficial effects of hPL on wound healing have been shown both in vitro as well as in small clinical trials in humans. In vitro, hPL has been shown to promote skin tissue repair (keratinocyte epithelialization and regulation of fibroblast matrix deposition). hPL has also shown positive effects in vitro on the viability, proliferation, migration, angiogenesis, intracellular pathways activation and inflammatory response of four different human cell types involved in the different phases of wound healing: monocytes, endothelial cells, fibroblasts and keratinocytes. A preliminary clinical study in seven patients with oral mucositis refractory to other therapies has shown preliminary safety, tolerance and effectiveness. In addition, human studies evaluating the topical application of individual growth factors has been disappointing, suggesting that wound healing may be dependent on the concerted effect of multiple growth factors. This data supports the rationale and likelihood of success of hPL as a therapeutic agent that can provide signaling cues for improving tissue viability and initiating tissue repair for wound healing. Growth factors work synergistically in their natural context, and the simultaneous delivery of multiple growth factors via the use of hPL is likely to optimize therapy. This would apply to both acute wounds and to chronic wounds. hPL is commercially available.

The present disclosure contemplates dressings, for example a bandage, upon which hPL, along with other therapeutic agents, can be applied. This increases the clinical utility of the dressing, and reduces the size, weight, and number of different medical supplies that a person would need to carry. This also makes it easier to apply the various therapeutic agents, and would be appropriate for a broad range of injuries (e.g. thermal burns, acute open wounds due to avulsion, laceration, or de-gloving), and also reduces the number of medical treatments that must be applied at the point/time of injury before the patient is transported to a medical care facility. In particular embodiments, the dressing comprises a delivery vehicle and hPL. The dressing can also include an antimicrobial agent, a hemostatic agent, and a binder, in any desired combination. A homogeneous mixture of these various ingredients can be used to form the dressing.

For purposes of this disclosure, a dressing that includes a substrate can be considered a bandage. Many different kinds of substrates are contemplated for the bandage. Desirably, the substrate is flexible, so that the bandage can conform to the shape of the wound to which it is applied. The present disclosure specifically contemplates the use of woven or non-woven gauze as a substrate in some embodiments. The non-woven gauze is generally a fibrous substrate. For purposes of this disclosure, similar structures such as mesh or sponge should be considered as falling within the scope of the word "gauze." The gauze is a light open mesh with multiple openings/pores that can readily absorb liquid. Gauze is also relatively thin, and can be considered as having only an upper surface and a lower surface. Gauze can be rolled up or folded up as desired for easy packing. During use, the gauze can be folded, balled up, or packed into the wound. In other embodiments, the substrate can be allograft, autograft, or xenograft tissue. When delivered using other naturally or artificially derived delivery agents such as collagen, alginate, cellulose or silicone, hPL can be delivered to the wound bed topically in form of a powder or a bandage.

In other embodiments, the delivery vehicle is a hydrogel. A hydrogel is a crosslinked polymer network that has hydrophilic groups, as a result of which water can be absorbed in large amounts, forming a colloidal gel. The crosslinked polymer network itself is referred to herein as the hydrogel matrix. The hydrogel matrix may comprise any suitable natural or artificial material, such as carboxymethylcellulose, collagen, fibrin, alginate, poly(lactic-co-glycolic acid), or polyethylene glycol, and can be a mixture of multiple materials if desired. The selection of the matrix can depend on the desired release kinetics, degradation rate, pore/fiber size, and mechanical properties. The matrix is then swelled in a liquid (i.e. gelled) to obtain the hydrogel. For example, the liquid can be a buffered saline such as phosphate buffered saline(PBS), and can have a pH of about 4 to about 9. The gelling can occur at any suitable temperature, for example from about 25° C. to about 37° C. The gelling that forms the hydrogel can occur over any needed time period. The gelling can be instantaneous, or the gelling can be delayed for up to 168 hours (one week). A hydrogel is useful for protecting growth factors from a proteolytic environment, sustaining their release and activity overtime, and minimizing their systemic absorption. As such, this delivery vehicle is particularly considered for use in chronic wounds such as diabetic foot ulcers. It is noted that the texture of the hydrogel can vary depending on the amount of liquid contained within the matrix. The hydrogel can be relatively stiff, or can have a creamy texture.

Any antimicrobial agent can be used in the dressings of the present disclosure, for the purpose of reducing or preventing bacterial infection of the wound to which the dressing is applied. In specific embodiments, the antimicrobial agent contains silver. Specifically contemplated silver-containing antimicrobial agents include silver sulfadiazine, silver nitrate, or silver chloride. In other embodiments, the antimicrobial agent is iodine, chlorhexidine, bacitracin, ciprofloxacin, gentamycin, honey. The antimicrobial agent can be present in therapeutically effective amounts.

Any antifungal agent can also be used in the dressings of the present disclosure, for the purpose of reducing or preventing fungal growth in the wound to which the dressing is applied. Examples of antifungal agents include polyenes like amphotericin B, candicidin, natamycin, and nystatin; imidazole, triazole, and thiazoles such as clotrimazole, ketoconazole, miconazole, fluconazole, itraconazole, terconazole, and abafungin; allylamines such as amorolfin, butenafine, naftifine, and terbinafine; tolnaftate, griseofulvin, flucytosine, undecylenic acid, and crystal violet. The antifungal agent can be present in therapeutically effective amounts.

A hemostatic agent may also be used in the dressings of the present disclosure. When brought into contact with blood, the hemostatic agent promotes clotting. It is specifically contemplated that the dressing contains a hemostatic agent such as kaolin, chitosan, a zeolite, or a styptic. Kaolin is a clay having the chemical formula $Al_2Si_2O_5(OH)_4$, and is also known as kaolinite. Chitosan is a linear polysaccharide composed of randomly distributed β-(1-4)-linked D-glucosamine units and N-acetyl-D-glucosamine units. A zeolite is a microporous, aluminosilicate mineral. These materials promote clotting. For example, kaolin activates Factor XIII in the presence of kallikrein and kininogen. Factor XIII activates Factor XI, resulting in a fibrin clot. A styptic causes tissue to contract, which seals blood vessels and reduces bleeding. Exemplary styptics include anhydrous aluminum sulfate, potassium permanganate, zinc oxide, and zinc sulfate. The hemostatic agent may be in the form of a powder or particle. The hemostatic agent can be present in therapeutically effective amounts.

A binder may be used to help bind the other ingredients (i.e. hPL, antimicrobial agent, hemostatic agent) to each other or to the delivery vehicle, particularly when the delivery vehicle is a dry substrate (such as non-woven gauze). This produces a cleaner product when the dressing is removed from its packaging to be used, and provides more of the therapeutic agents to the wound (instead of being left in the packaging). Specifically contemplated binders include polyethylene glycol, glycerol, casein, acacia gum, xanthan gum, corn starch, wheat starch, cellulose, gelatin, pectin, chitosan, dextran, or albumin. Besides glycerol, other polyols like sorbitol, xylitol, or polydextrose can also be used. Some additional processing steps may be needed to cause crosslinking of the binder. The binder can be present in effective amounts.

A platelet activating component may also be included in the dressing to promote coagulation. This component activates platelets, which occurs after adhesion of the platelet to the sub-endothelium. Exemplary platelet activating components include calcium salts such as $CaCl_2$); adenosine diphosphate (ADP); phospholipase C beta2; inositol 1,4,5-trisphosphate; serotonin; thromboxane $A_2$; platelet activating factor; von Willebrand factor (vWF); platelet factor 4; and phospholipase $A_2$. Such components are present in a physiologically effective amount.

A fibrinogen activating component may also be included in the dressing to promote coagulation. This component causes fibrinogen to be converted to fibrin. Exemplary fibrinogen activating components include thrombin, batroxobin, and similar enzymes.

In specific embodiments, the dressing is in the form of a bandage, where the delivery vehicle is a substrate. In particularly contemplated embodiments, the bandage is formed from the substrate and the hPL, and does not contain an antimicrobial agent or hemostatic agent. In other embodiments, the bandage is formed from a substrate that has hPL and an antimicrobial agent, but does not have a hemostatic agent. In still other embodiments, the bandage is formed from a substrate that has hPL, an antimicrobial agent, and a hemostatic agent applied thereto. A binder may or may not be used in these embodiments. The substrate is formed from a homogeneous mixture of the desired ingredients.

Such bandages of the present disclosure can be made by multiple different methods. In these methods, the hPL is typically provided in a powder form. Removal of water from hPL increases the stability of labile growth factors and enables easy control over total protein dosing. The lyophilization of sera and serum proteins is well documented, and the high concentration of proteins in hPL can provide a stabilizing effect to preserve maximal activity.

For substrates such as woven or non-woven gauze, it is contemplated that a solution is formed. The substrate is then combined with the solution. For example, the substrate can be immersed in the solution, or the substrate could be sprayed with the solution. Because the hPL can be affected by high temperatures, the impregnated substrate is subsequently frozen. It is contemplated that temperatures below −70° C. are obtained, for example by exposure to liquid nitrogen. Water is then removed by lyophilization, where the pressure is reduced to allow the water to sublimate directly from the solid phase to the gas phase. Depending on the desired structure for the bandage, the substrate can be combined or exposed to multiple different solutions to form the desired structure.

Additional processing steps may occur when human platelet lysate (hPL) is not present on the substrate, for example drying using high heat, which would otherwise be contraindicated because heat would reduce the activity of the hPL. For example, in some embodiments, it is contemplated that a hemostatic agent is first applied to the substrate, and then the hPL is applied to the substrate. In such embodiments, a first solution could be formed by adding a binder and a hemostatic agent (e.g. kaolin) to water to form a slurry. The slurry is then applied to the substrate, for example by spraying, dipping, or immersion. The hemostatic agent is bound to the substrate by the binder. Additional steps may be needed to cause crosslinking of the binder. Unbound material can be washed off. The substrate is then dried, for example by exposing the substrate to high heat, such as by blowing hot air, or by exposure to radiation, or by removing moisture from the air around the substrate, or by freezing and lyophilization. The result is a substrate impregnated with the hemostatic agent. The hemostatic agent-impregnated substrate is then exposed to a second solution containing the hPL. The substrate is then frozen and lyophilized. The resulting bandage structure can be described as a substrate having a layer of hemostatic agent and a layer of hPL thereon as an outermost layer. If desired, the bandage can then be sterilized using radiation, such as gamma radiation, or using ultraviolet light (wavelength of about 10 nm to about 380 nm).

Alternatively, if a single layer containing multiple ingredients is desired, all of the ingredients (i.e. hPL, antimicrobial agent, hemostatic agent, binder) would be combined into a single solution. The substrate and the solution would be combined, for example by immersion. The impregnated substrate is then frozen and lyophilized. This results in a substrate having a single layer thereon that contains the multiple ingredients.

FIG. 1 is a cross-sectional diagram of a dressing/bandage that comprises a substrate and hPL applied thereon. The bandage 100 includes a substrate 110, which is illustrated here as being a non-woven gauze having an upper surface 112 and a lower surface 114. The hPL is illustrated as circles 120, and is illustrated as being present on the upper surface and the lower surface, and also being impregnated within the substrate 110.

FIG. 2 is a cross-sectional diagram of a dressing/bandage 100 that comprises a substrate and both hPL and a hemostatic agent applied thereon. Here, the hemostatic agent is present as a first layer 130 on the substrate 110, and the hPL is present as a second layer 132 upon the first layer 130. The hPL is an outermost layer of the substrate. This particular figure (and also the following figures) does not show the layers of hemostatic agent and hPL on the individual fibers of the substrate, as may happen, and does not illustrate the impregnation that can occur within the substrate.

FIG. 3 is a cross-sectional diagram of a dressing/bandage 100 that comprises a substrate 110 and both hPL and an antimicrobial agent applied thereon. Here, the hPL is represented by circles 120, and the antimicrobial agent is represented as diamonds 122, and both ingredients are present and uniformly dispersed throughout the same layer 140.

Figures 4, 5, 6:
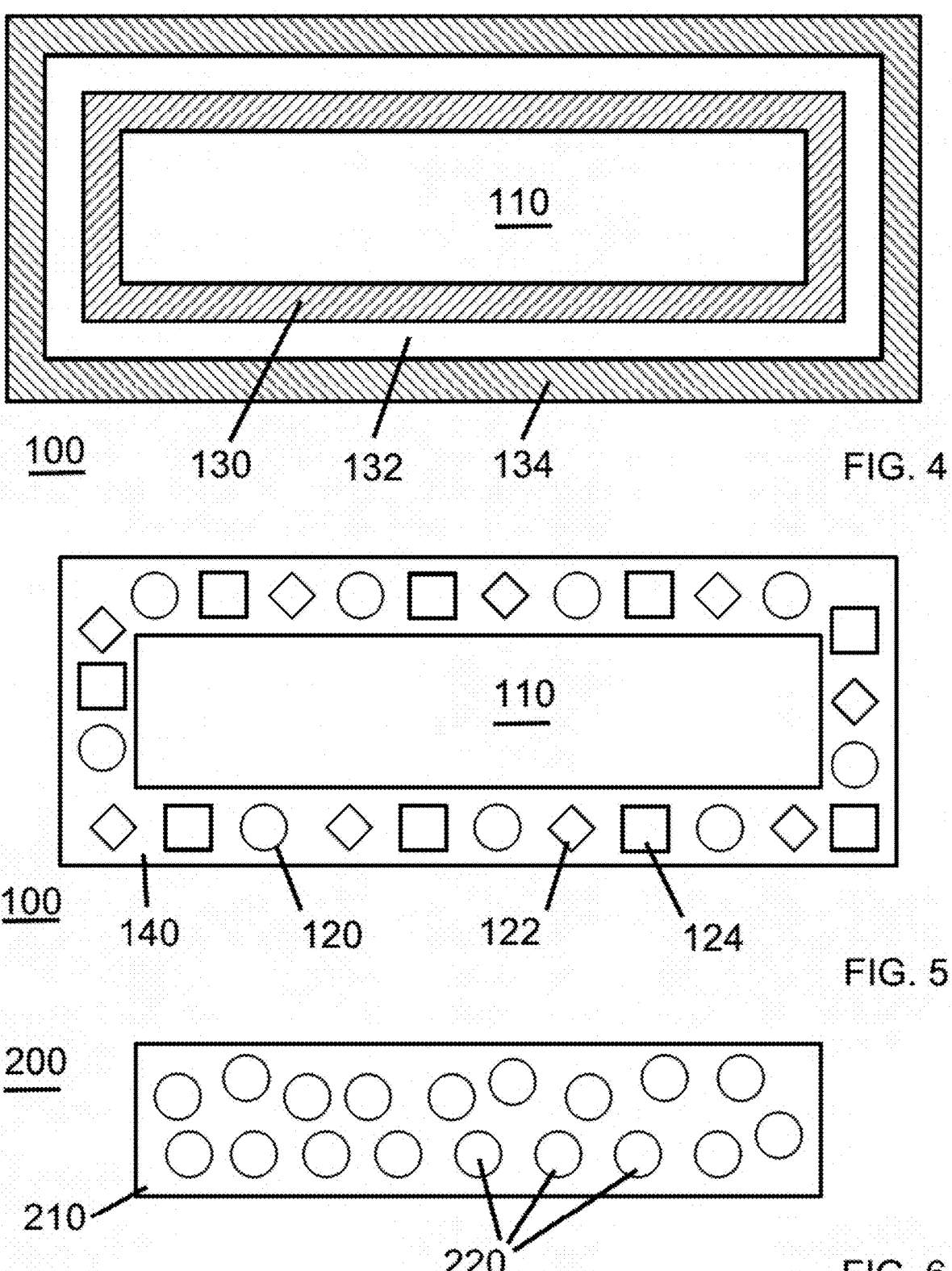
FIG. 4 is a cross-sectional diagram of a dressing that comprises a substrate and has human platelet lysate, a hemostatic agent, and an antimicrobial agent applied thereon. In this embodiment, three separate layers are present upon the substrate.
FIG. 5 is a cross-sectional diagram of a dressing that comprises a substrate and has hPL, a hemostatic agent, and an antimicrobial agent applied thereon. In this embodiment, the three ingredient are present in the same layer.
FIG. 6 is a cross-sectional diagram of a dressing that comprises a substrate and hPL present within the hydrogel.

FIG. 4 is a cross-sectional diagram of a dressing/bandage 100 that comprises a substrate and has hPL, a hemostatic agent, and an antimicrobial agent applied thereon. In this embodiment, three separate layers are present upon the substrate 110. The hemostatic agent is first layer 130, the antimicrobial agent is second layer 132, and the hPL is in the third and outermost layer 134.

FIG. 5 is a cross-sectional diagram of a dressing/bandage 100 that comprises a substrate 110 and has hPL, a hemostatic agent, and an antimicrobial agent applied thereon. In this embodiment, the three ingredients are present in the same layer 140. The hPL is represented by circles 120, the antimicrobial agent is represented as diamonds 122, and the hemostatic agent is represented by squares 124.

In embodiments where the delivery vehicle is a hydrogel, the dressing can be formed by mixing lyophilized hPL (in powder form) with the hydrogel matrix (generally also in powder form). It is contemplated that the weight ratio of the hPL to the hydrogel matrix may be from about 0.25% to about 90%, and in more particular embodiments about 0.5% to about 2% (w/w). The hydrogel matrix is then gelled by bathing the matrix with a buffered saline at a pH of about 4 to about 9, or about 6 to about 8, such as pH 7.4. The matrix is incubated at an appropriate temperature (e.g. 37° C.) for an appropriate time to obtain the hydrogel containing hPL. The gelling can occur up to a week after the hPL and the matrix material are mixed together. If desired, the hydrogel can be applied to a support structure, such as a Tegaderm® transparent film, for easier handling.

FIG. 6 is a cross-sectional diagram of a dressing 200 that comprises a hydrogel 210 and hPL 220 applied thereon. Here, the hPL (represented by circles 220) is present within the hydrogel.

The resulting dressings contain hPL, which is a bioactive coating that provides signaling cues to improve tissue viability and initiate tissue repair for wound healing. Hemostasis and infection control can also be addressed by providing clotting and antimicrobial agents in a conformal barrier to reduce fluid loss. The dressings of the present disclosure can be used with a variety of conformal dressings (e.g. occlusive dressings) that will further reduce the loss of fluid through evaporation. Desirably, the dressing acts as an all-in-one dressing that maintains tissue viability if applied to a thermal burn, chemical burn, or open wound within 72 hours of the injury. The dressing should have a long shelf life and be usable over a broad range of environmental conditions, e.g. temperatures of −20° C. to +43° C.

The dressings can also act as a platform for sustained delivery of platelet-derived growth factors. In this regard, growth factors rapidly degrade in the proteolytic environment of a chronic wound, which may result in insufficient concentration of the growth factors over time, which can affect treatments that are only periodically applied (e.g. becaplermin). Second, as previously noted, the concurrent application of multiple growth factors may be required to enable optimal healing and wound closure. Successful wound closure is an intricate process that involves numerous growth factors and cytokines that stimulate ingrowth and proliferation of multiple cell types, including normal human dermal fibroblasts (NHDFs) and neonatal human epithelial keratinocytes (NHEKs). The ability for human mesenchymal stromal cells (hMSCs) to regenerate blood vessels is also vital to wound revascularization of diabetic foot ulcers. It is believed that application of hPL in dressing form will accelerate wound closure of diabetic foot ulcers as well.

In use, the dressing contacts the wound, and the hPL comes into direct contact with the tissues of the wound. Growth factors, attachment factors, and enzymes are thus delivered to the wound to accelerate the healing thereof.

The dressings of the present disclosure containing hPL (hPL) could also be used for post-surgical wounds, or be combined with another bandage or polymer. The dressing, when in the form of a bandage, could be used as a dermal plug to close a wound fissure. The dressing could also be used for wound healing of an allograft, an autograft, a xenograft, or a synthetic graft.

In other embodiments, the dressings include a delivery vehicle that is in the form of a powder. The powdered delivery vehicle is mixed with the hPL, and then packaged in powder form. For example, the delivery vehicle could be any suitable natural or artificial material that could form a hydrogel, such as carboxymethylcellulose, collagen, fibrin, alginate, poly(lactic-co-glycolic acid), or polyethylene glycol. The powdered dressing could be deposited on a wound, and the exudate from the wound would provide the liquid needed to form the hydrogel. In such embodiments, it is contemplated that the weight ratio of the hPL to the delivery vehicle could range from about 9:1 to about 1:399 (i.e. 0.25 wt % to 90 wt % of hPL), including from about 4:1 to about 1:4, or from about 2:1 to about 1:2. Once exposed to liquid, the relative amount of hPL in the dressing would decrease as the liquid is absorbed.

In still other embodiments, the delivery vehicle is in the form of a liquid carrier. The liquid can be water, mineral oil, or another suitable material that is liquid at room temperature. In these forms, especially those containing high amounts of liquid carrier, the dressing could be injected into a desired location of the body.

In particular embodiments where the delivery vehicle is a liquid carrier, the dressing can also contain a surfactant (i.e detergent), and is in the form of a shampoo. The surfactant can be an anionic, nonionic or amphoteric surfactant. The shampoo can contain about 10 wt % to about 15 wt % of the surfactant. The shampoo is usually at least 70 wt % water. The shampoo may contain from about 0.25 wt % to about 90 wt %, and in more particular embodiments about 0.5% to about 2% of the hPL.

Exemplary anionic surfactants include alkyl sulphates, alkyl ether sulphates, alkaryl sulphonates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate.

Examples of suitable nonionic surfactants may include condensation products of aliphatic primary or secondary linear or branched chain alcohols or phenols with alkylene oxides, usually ethylene oxide. The alkyl groups generally contain from 8 to 18 carbon atoms and may be unsaturated. The alkylene oxide groups are usually ethylene oxide or propylene oxide units, and usually contain 6 to 30 units per molecule.

Suitable amphoteric surfactants can include alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms. Examples include lauryl amine oxide, cocodimethyl sulphopropyl betaine, lauryl betaine, cocamidopropyl betaine and sodium cocamphopropionate.

In other embodiments where the delivery vehicle is a liquid carrier, the dressing is in the form of a cream. The cream contains less than 25 wt % water and contains at least 50% of a wax, which is used as a thickening agent. The wax can be a hydrocarbon or a paraffin, or could be beeswax. The wax may be in the form of small crystals. The cream may contain from about 0.25 wt % to about 90 wt %, and in more particular embodiments about 0.5% to about 2% of the hPL. It is contemplated that such creams could be useful for topical application.

In other embodiments where the delivery vehicle is a liquid carrier, a gelling agent is present, and the dressing is in the form of a gel. The gelling agent provides stiffness to the liquid solution or dispersion. Exemplary gelling agents include acacia, alginic acid, bentonite, carbomers, carboxymethyl cellulose, ethylcellulose, gelatin, hydroxyethyl cellulose, hydroxypropyl cellulose, magnesium aluminum silicate, methylcellulose, poloxamers, polyvinyl alcohol, sodium alginate, tragacanth, and xanthan gum. An acid or base may also be added to adjust the pH as needed. The gelling agent is usually present in the amount of 0.5 wt % to 10 wt % of the gel. It should be noted that the difference between a hydrogel is a type of gel. The cream may contain from about 0.25 wt % to about 90 wt %, and in more particular embodiments about 0.5% to about 2% of the hPL.

In yet other potential embodiments, the dressing is in the form of a foam or aerosol, where the delivery vehicle is a pressurized gas, i.e. a propellant. The dressing would be contained in a can with a nozzle spray. Suitable gases that could be used for the propellant could include hydrocarbons such as propane, n-butane and isobutane; dimethyl ether and methyl ethyl; nitrous oxide; carbon dioxide; nitrogen; air; and hydrofluoroalkanes (HFA) such as HFA 134a (1,1,1,2,-tetrafluoroethane) or HFA 227 (1,1,1,2,3,3,3-heptafluoropropane).

As a cosmeceutical, it is contemplated that dressings in the form of bandages, shampoos, foams, or creams could be used to promote hair regrowth, for filling wrinkles, for treating atrophic acne scars, or for treating sunburns. In these embodiments used for skin care, the dressing (in any form) could also contain hyaluronic acid, which is a well-known component of the extracellular matrix. It is possible such dressings could be used to expedite healing after cosmetic surgery, such as facelifts or hair plug implantation.

It is also contemplated that the dressings could be used in treating critical limb ischemia, preventing amputations, or in post amputation applications for tissue preservation, maintaining the health of the stump, and potentially for expediting nerve repair. The dressings could also be used for repairing orthopedic wounds and soft tissues, such as the rotator cuff, cartilage, the tendon, or the meniscus. In such applications, the dressing could potentially be implanted or injected inside the body. The dressing (particularly the hydrogel form) could be applied as a topical treatment after post-radiation treatment, a mastectomy, or upon colo/rectal ulcers or hemmorhoids. hPL delivered by bandage might enhance nerve repair in conditions like Lou Gehrig's disease. The bandages could also be used as a patch for providing a body building supplement or performance enhancer. The bandages could also be used to treat the symptoms of musculoskeletal disorders, like muscular dystrophy. The bandages could also be used for improving sexual health, incontinence, or other problems related to the reproductive organs of both men and women. These share a common trait of being related to muscle tone, and hPL could be useful in that regard.

The aerosolized form of hPL could potentially be nebulized for delivery to the lungs. This could be used to treat acute lung injuries (ALI), chronic obstructive pulmonary disease (COPD), or asthma. hPL could be applied intranasally (as a nasal spray) to treat concussions, traumatic brain injury (TBI), sinus infections, or anosmia, or for preventing colds. hPL could also be delivered orally to treat ulcers or to enhance post radiation salivary gland regeneration, as a mouthwash or throat spray, or used to enhance dental regeneration as either a filler or for gum repair. The hPL could be used for dental pulp applications to treat various conditions of the jaw, bone, joints, nerves, or the roots, such as the temporomandibular joint (TMJ). In the form of eye drops or eye gels, hPL could be used to treat dry eye, ulcers, lesions, or abrasions of the eye, or be used as a post-surgery application/treatment.

The discussion herein has been specifically directed to human platelet lysate (hPL). However, it is contemplated that the platelet lysate could also be bovine, equine, porcine, ovine, caprine, canine, feline, cervine, lupine, ursine, or simian, and the discussion herein should also be interpreted as applying to platelet lysate originating from other animals/species than humans.

The present disclosure will further be illustrated in the following non-limiting three sets of working examples, it being understood that these examples are intended to be illustrative only and that the disclosure is not intended to be limited to the materials, conditions, process parameters and the like recited herein. All proportions are by weight unless otherwise indicated.

Example 1

A preliminary bandage prototype was prepared by incubating 35 mm diameter circular disks of kaolin-impregnated gauze in human platelet lysate for 4 minutes at room temperature. The soaked gauze was immediately lyophilized. The initial in vitro hemostatic properties of the samples were measured by thromboelastography. The initial growth factor release characteristics of the samples were quantified using enzyme-linked immunosorbent assay (ELISA) with platelet-derived growth factor-BB (PDGF-BB), a pro-survival and angiogenic growth factor. The size, shape and mechanical strength of the samples before and after impregnation with hPL were also monitored.

Figures 7A, 7B, 7C, 7D, 7E:
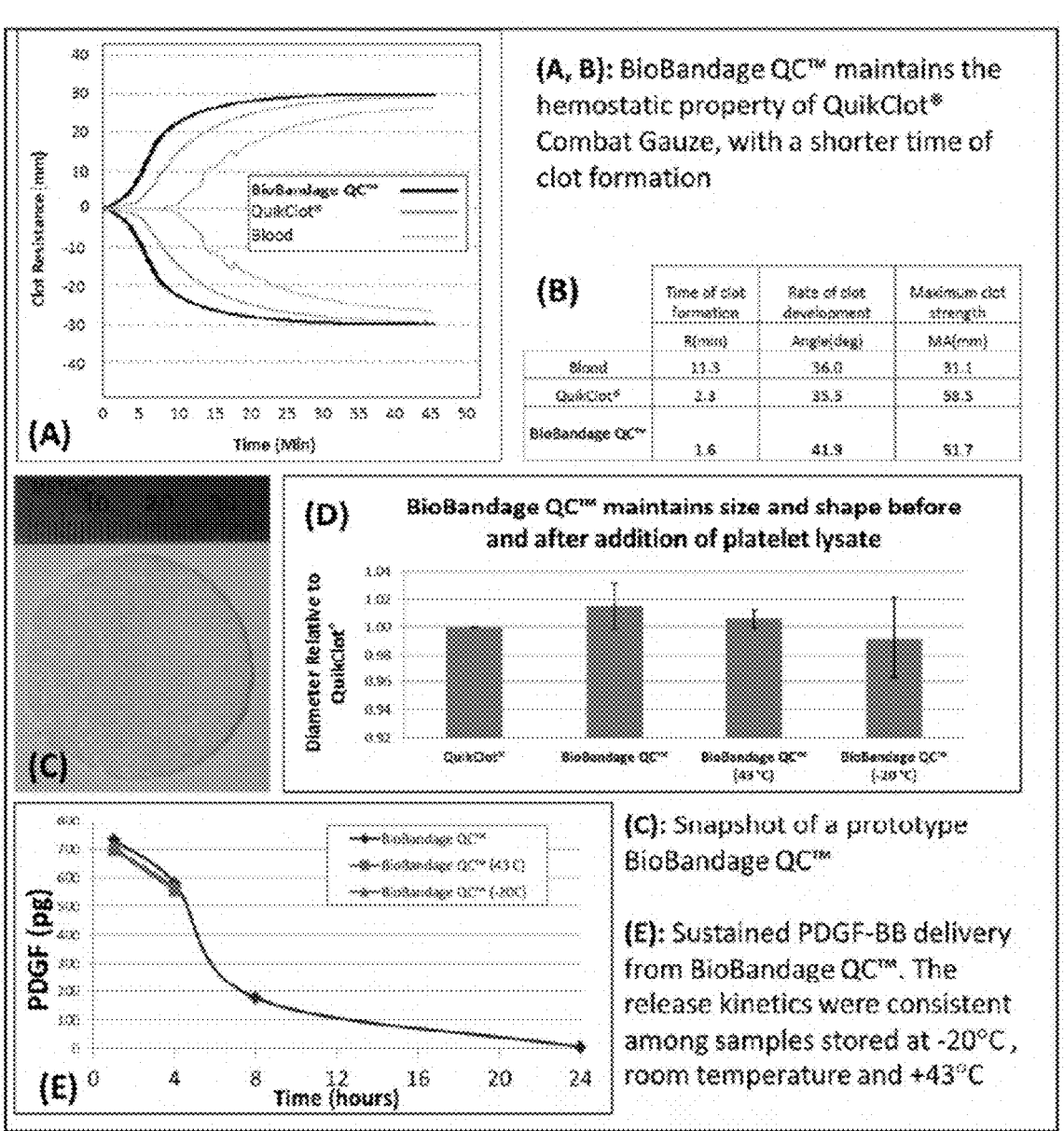
FIGS. 7A-7E illustrate data from an experiment comparing (i) a kaolin-hPL bandage ("BioBandage QC™") against (ii) a kaolin bandage ("QuickClot®") and (iii) blood.

FIGS. 7A-7E show the results. In these tests, blood was used as the control and baseline. "QuickClot®" refers to kaolin-impregnated gauze, and BioBandage QC™ refers to gauze that is impregnated with both kaolin and hPL. As seen in FIG. 7A and FIG. 7B, the addition of hPL did not reduce hemostatic capability. The BioBandage QC™ showed a lower time of clot formation, similar rate of clot development, and slightly lower maximum clot strength compared to the QuikClot®. FIG. 7C is a picture of the BioBandage QC™ having hPL applied. As seen in FIG. 7D, the addition of hPL did not change the size, shape, fluid retention ability, or mechanical strength of the BioBandage QC™ relative to the QuikClot®, even at extreme temperatures (both hot and cold). A sustained release of hPL-derived PDGF-BB was also found from the BioBandage QC™, even at extreme temperatures, as seen in FIG. 7E. This data provides initial proof-of-concept for development of BioBandage QC™ as a delivery vehicle with an internal bioactive coating that can combine a sustained delivery of endogenous growth factors with the hemostatic property of kaolin.

Example 2

To verify that lyophilized hPL still maintained growth factor activity, a cell culture supplement study was performed for three important dermal wound healing cell types: human mesenchymal stromal cells (MSCs), normal human dermal fibroblasts (NHDF), and neonatal human epidermal keratinocytes (NHEK). An aliquot of PLUS™ hPL was divided in two. One half of the aliquot was lyophilized and resuspended in an equal volume of deionized water, while the other half was frozen and then thawed prior to use. Culture media for each cell type was supplemented with both forms of 5% hPL as well as 10% FBS (as baseline) and the cells were cultured for a single passage. Culture with either form of PLUS™ resulted in no difference in the doubling times for all three cell types, and trended towards faster doubling times compared with FBS. These results indicate that the growth promoting activity of PLUS™ hPL was unaffected by the lyophilization process.

Figure 8A:
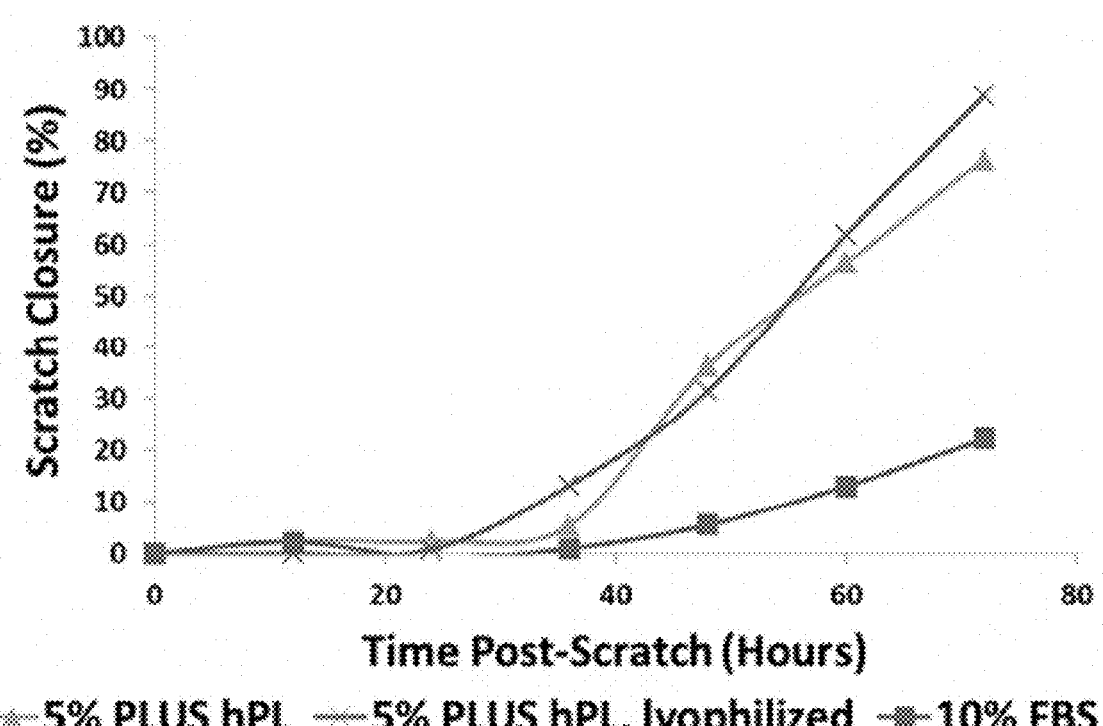
FIG. 8A is a graph showing percentage scratch closure versus time for three different cell cultures.
Figure 8B:
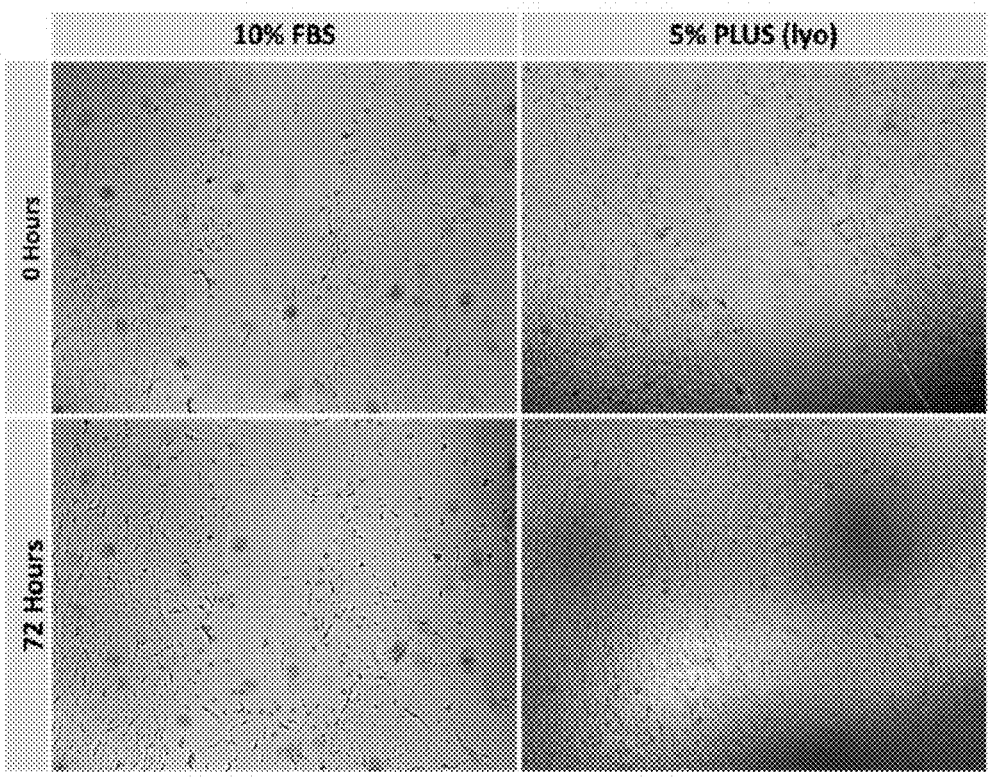
FIG. 8B is a set of four pictures showing the results of a scratch assay comparing (i) 10% fetal bovine serum (FBS) with 5% hPL at (ii) 0 hours and 72 hours.

Next, to evaluate the ability of the lyophilized hPL to stimulate NHDF migration, a scratch assay was performed. In this assay, a scratch was induced on the bottom of a confluent monolayer of NHDF and culture media was again supplemented with both forms of hPL as well as 10% FBS. The percentage scratch closure was calculated over time, and results are shown in FIG. 8A and FIG. 8B. As seen in FIG. 8A, the cultures with either form of 5% hPL resulted in a fourfold increase in the migration of NHDF after 72 hours, compared to the 10% FBS culture. FIG. 8B is a set of four pictures at 0 hours and 72 hours for 10% FBS and 5% hPL. These preliminary results indicate that the migration promoting activity of hPL is unaffected by the lyophilization process.

Example 3

Figure 9:
FIG. 9 is a picture of an hPL-collagen bandage after being hydrated with 0.9% saline, and shows the bandage is flexible and conformable to the surface of a wound.

Another bandage prototype was prepared by combining bovine collagen and hPL at 37° C. for one hour, pouring the solution into molds, freezing the solution, and finally lyophilizing it. By weight, the bandage was approximately 27% collagen (1% w/v collagen solution) and 73% hPL. The resultant bandage was shelf stable. FIG. 9 is a picture of the bandage after being saturated with 0.9% saline, and shows the bandage is flexible and conformable to the surface of a wound.

The bandage demonstrated initial biocompatibility, safety, and non-toxicity testing. The bandage passed the following ISO 10993 tests: (A) Agar Diffusion cytotoxicity Test (mouse fibroblast L929 culture); (B) Kligman Maximization/Sensitization Test (guinea pigs); (C) Acute Systemic Injection Test (mice); (D) 28 Day Sub-Acute Systemic Toxicity by Implantation (rats); (E) 2 Week Intramuscular Implantation Test (rabbits); and (F) 4 Week Intramuscular Implantation Test (rabbits).

Figures 10A, 10B, 10C, 11A, 11B, 11C:
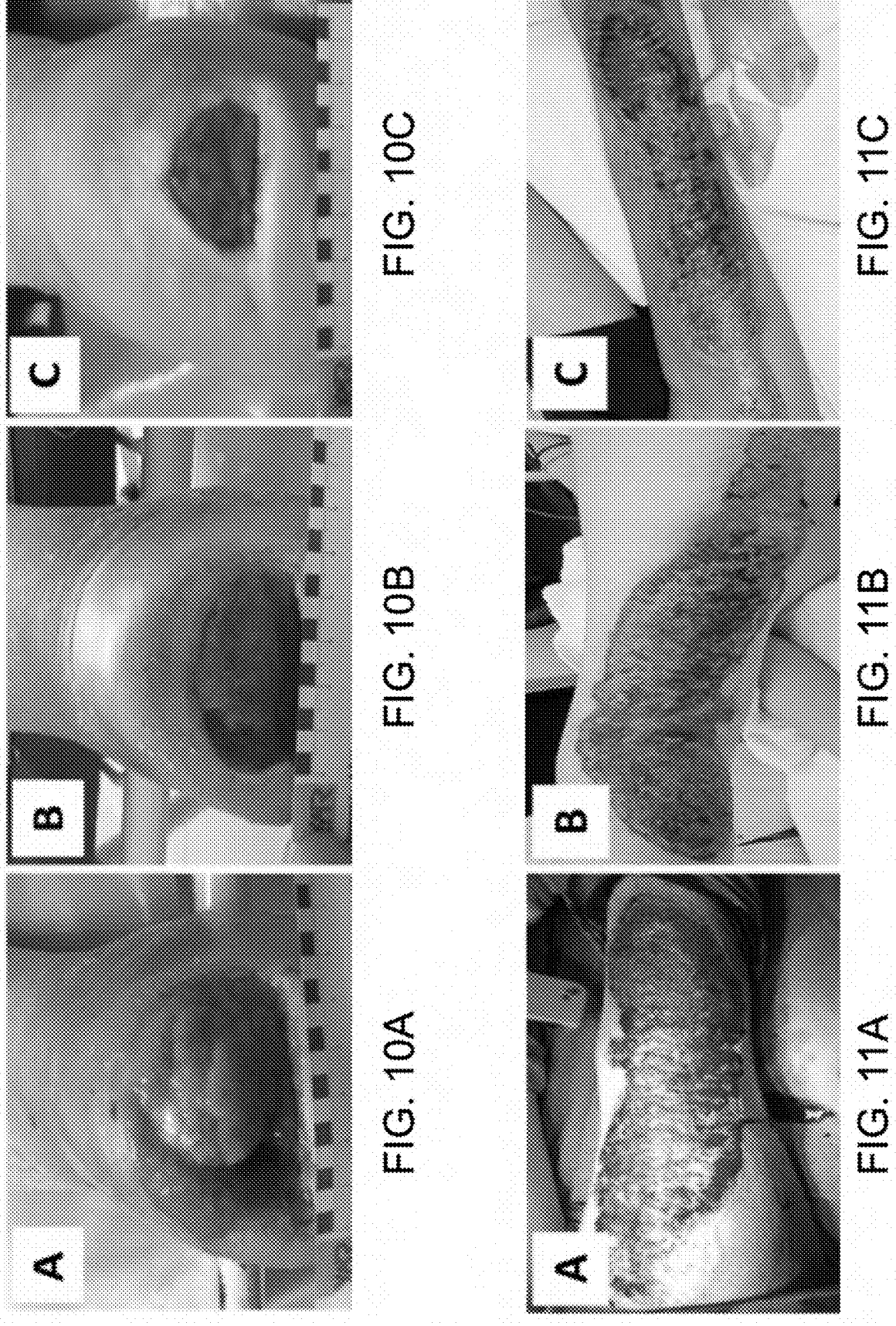
FIGS. 10A-10C are pictures of a 69 year old diabetic male with a non-healing diabetic foot ulcer. Multiple applications of an hPL-containing bandage (1% w/v collagen, 37% v/v hPL) were performed.
FIGS. 11A-11C are pictures of a 26-year old female with an extensive burn wound on the back of the thigh and the calf. Multiple applications of an hPL-containing bandage (1% w/v collagen, 37% v/v hPL) were performed.

The bandage also demonstrated initial safety in chronic and burn wounds. FIGS. 10A-10C are pictures of a 69-year old diabetic male with a non-healing diabetic foot ulcer. Multiple applications of an hPL-collagen bandage (1% w/v collagen, 37% v/v hPL) were applied. FIG. 10A is a baseline wound image. FIG. 10B is an image of the wound after 2 weeks of hPL-collagen bandage application. FIG. 10C is an image of the wound after 12 weeks of hPL-collagen bandage application to the wound.

FIGS. 11A-11C are pictures of a 26-year old female with an extensive burn wound on the back of the thigh and the calf. Multiple applications of an hPL-containing bandage (1% w/v collagen, 37% v/v hPL) were performed. FIG. 11A is a baseline picture. FIG. 11B is a picture after 5 days of hPL-collagen bandage application. FIG. 11C is a picture after 16 days of application.

Example 4

Preliminary studies were carried out to evaluate the ocular wound healing capabilities of hPL both in vitro and in vivo.

Figures 12A, 12B:
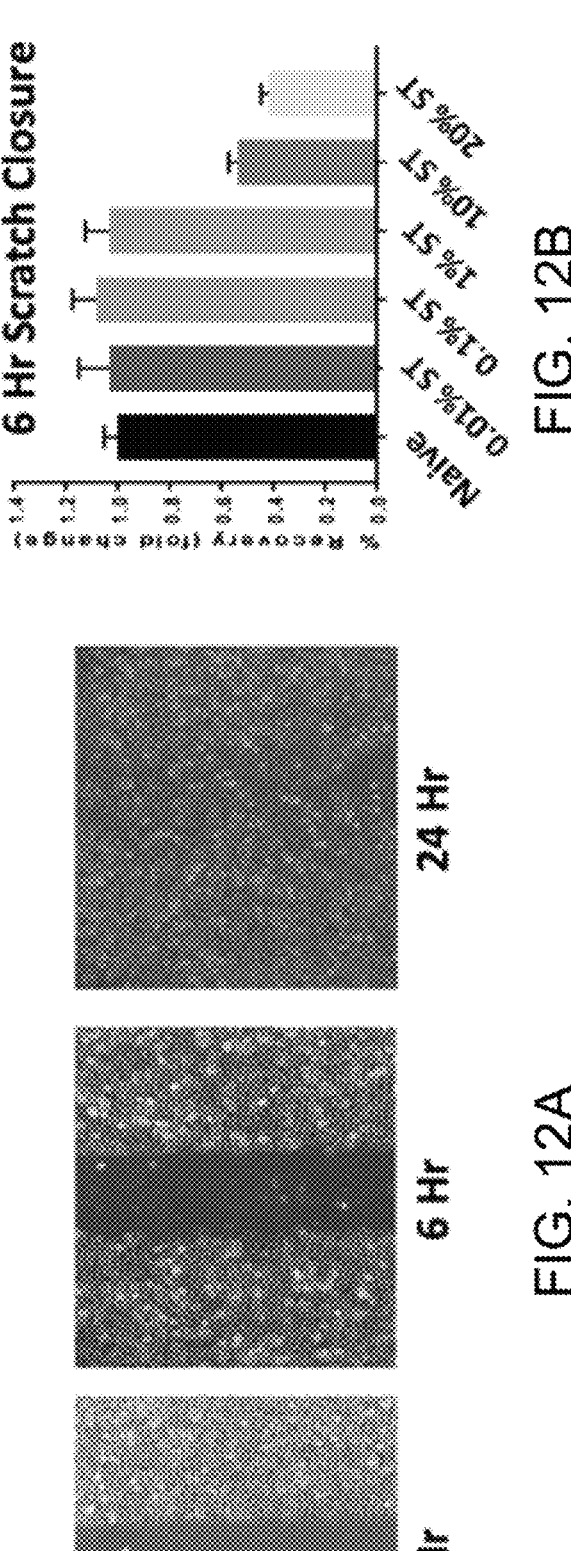
FIG. 12A is a set of three pictures showing wound healing response in a confluent monolayer culture of human corneal epithelial cells after 20% hPL is added to the cell culture medium. The three pictures are at 0 hours, 6 hours, and 24 hours.
FIG. 12B is a bar graph showing the scratch closure versus the hPL dosage. The closure is dose dependent. The y-axis is the % recovery in units of fold change, and runs from 0.0 to 1.4 in intervals of 0.2. A lower value is better, as it shows a faster healing of a simulated ocular epithelial wound. On the x-axis, from left to right, the x-axis is labeled Naïve, 0.01% ST, 0.1% ST, 1% ST, 10% ST, and 20% ST, where ST refers to the percentage of "supplemented treatment" of hPL that was present in the cell culture medium.

An in vitro scratch assay model was used, in which an ocular 'wound' was made by mechanically scraping a confluent monolayer culture of human corneal epithelial cells (HCECs). Different dosages of hPL were then applied. FIG. 12A is a set of three pictures showing wound healing response in a confluent monolayer culture of human corneal epithelial cells after 20% hPL is added to the cell culture medium. The three pictures are at 0 hours, 6 hours, and 24 hours. As seen here, by 24 hours, the scratches were completely closed.

FIG. 12B is a graph showing the scratch closure versus the hPL dosage after 6 hours. The graph shows that hPL stimulated wound healing responses in a dose-dependent manner. A dose as low as 10% hPL added to the culture medium led to significantly faster closure of scratches compared to the cell culture medium alone.

In preliminary in vivo studies, a guinea pig superficial ocular injury model was used. In this model, the corneal epithelium was carefully removed using a motorized foreign body and rust ring remover brush (Algerbrush II) after demarcating the cornea with a biopsy punch. hPL treatments were then applied via a custom designed ocular wound chamber that prevents the animals from scratching their eyes during the study and enables treatments to maintain continuous contact with the ocular surface.

Figure 13:
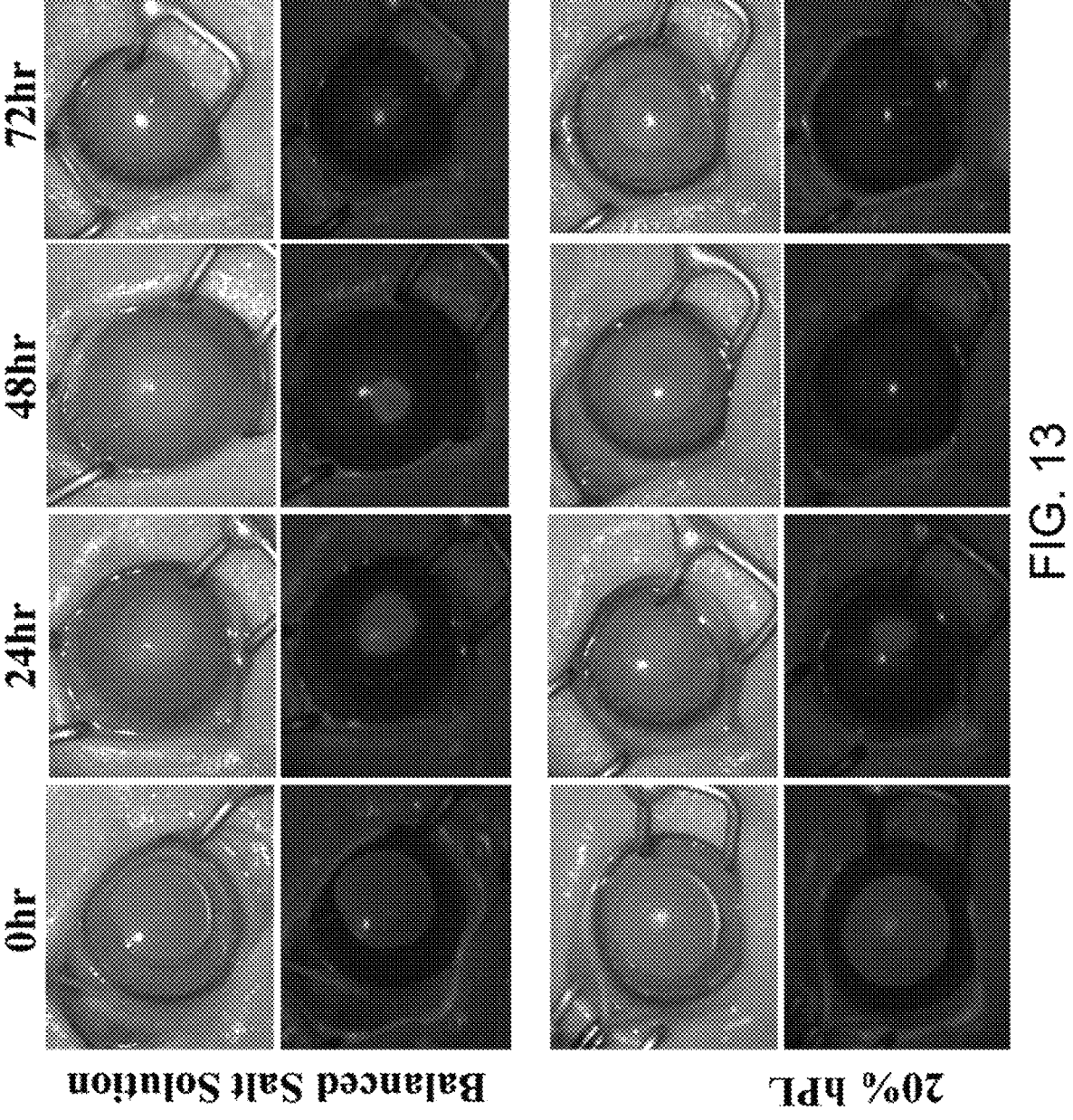
FIG. 13 is a set of 16 images, arranged in four rows and four columns, showing the effect of hPL on a corneal epithelial wound. The top two rows are results when a balanced salt solution is applied to the wound. The bottom two rows are results when a 20% hPL solution is applied to the wound. The second and fourth rows are fluorescein staining. The four columns are 0 hours, 24 hours, 48 hours, and 72 hours after application.

FIG. 13 is a set of 16 images, arranged in four rows and four columns, comparing the effect of a 20% hPL solution to a balanced salt solution on a corneal epithelial wound. The top two rows are results when a balanced salt solution is applied to the wound. The bottom two rows are results when a 20% hPL solution is applied to the wound. The second and fourth rows are fluorescein staining. As seen in the fluorescein stained images, a dose of 20% hPL demonstrated faster epithelial closure at 24 hours compared to the controls treated with a balanced salt solution. Complete closure with hPL was achieved by 48 hours, whereas the control required 72 hours.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A dressing, comprising:

a delivery vehicle; and platelet lysate on a surface of the delivery vehicle; and a poloxamer;

wherein the delivery vehicle is a powder, and wherein the powder is carboxymethylcellulose, collagen, fibrin, poly (lactic-co-glycolic acid), or polyethylene glycol; and wherein the dressing does not include a fiber or gauze substrate.

2. The dressing of claim 1, wherein the dressing further comprises an antimicrobial agent.

3. The dressing of claim 2, wherein the antimicrobial agent contains silver; or wherein the antimicrobial agent is iodine, chlorhexidine, bacitracin, ciprofloxacin, gentamycin, or honey.

4. The dressing of claim 1, wherein the dressing further comprises a hemostatic agent, wherein the hemostatic agent is kaolin, chitosan, a zeolite, or a styptic; or wherein the dressing further comprises a binder, wherein the binder is glycerol, casein, arabic gum, xanthan gum, corn starch, wheat starch, cellulose, gelatin, pectin, chitosan, dextran, or albumin.

5. The dressing of claim 1, wherein the dressing further comprises an antifungal agent.

6. The dressing of claim 2, wherein the antimicrobial agent is silver sulfadiazine, silver nitrate, or silver chloride.

7. The dressing of claim 4, wherein the styptic is anhydrous aluminum sulfate, potassium permanganate, zinc oxide, or zinc sulfate.

* * * * *